(12) United States Patent
Lacey

(10) Patent No.: US 12,280,218 B2
(45) Date of Patent: Apr. 22, 2025

(54) SYSTEMS AND METHODS FOR AN ULTRASONICALLY DRIVEN ANESTHETIC VAPORIZER

(71) Applicant: General Electric Company, Schenectady, NY (US)

(72) Inventor: Joseph James Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 307 days.

(21) Appl. No.: 18/066,721

(22) Filed: Dec. 15, 2022

(65) Prior Publication Data

US 2023/0123214 A1  Apr. 20, 2023

Related U.S. Application Data

(62) Division of application No. 16/184,678, filed on Nov. 8, 2018, now Pat. No. 11,541,199.

(51) Int. Cl.
*A61M 16/18* (2006.01)
*A61M 16/00* (2006.01)
*A61M 16/20* (2006.01)

(52) U.S. Cl.
CPC ........ *A61M 16/18* (2013.01); *A61M 16/0003* (2014.02); *A61M 16/024* (2017.08); *A61M 16/202* (2014.02); *A61M 16/208* (2013.01); *A61M 2016/0036* (2013.01); *A61M 2202/048* (2013.01); *A61M 2205/10* (2013.01); *A61M 2205/15* (2013.01); *A61M 2205/3327* (2013.01); *A61M 2205/3368* (2013.01); *A61M 2205/3389* (2013.01); *A61M 2205/36* (2013.01); *A61M 2205/3633* (2013.01); *A61M 2206/20* (2013.01)

(58) Field of Classification Search
CPC ............. A61M 16/18; A61M 16/0003; A61M 16/202; A61M 16/021–024; A61M 16/208; A61M 2016/0036; A61M 2202/048; A61M 2205/10; A61M 2205/15; A61M 2205/3327; A61M 2205/3368; A61M 2205/3389; A61M 2205/36; A61M 2205/3633; A61M 2206/20; A61M 16/203; A61M 2205/368; A61M 2205/3653; A61M 2205/505; A61M 16/183; A61M 2230/205; A61M 16/12; A61M 2230/42; A61M 2016/0039; A61M 2016/0042; A61M 16/009; A61M 16/22; A61M 16/1015; A61M 16/127; A61M 11/005; A61M 16/109; A61M 2016/1035; A61M 16/104; A61M 16/1085; B05B 17/00–085
USPC .......................... 128/203.13, 203.26, 203.27
See application file for complete search history.

(56) References Cited

U.S. PATENT DOCUMENTS

2016/0151599 A1*  6/2016  Korneff ............... A61M 16/109
                                                          128/203.26
2019/0099581 A1*  4/2019  Kuzelka .............. A61M 16/024

* cited by examiner

*Primary Examiner* — Elliot S Ruddie

(57) ABSTRACT

Methods and systems are provided for delivering anesthetic agent to a patient. In one embodiment, an anesthetic vaporizer includes a sump configured to hold a liquid anesthetic agent; an ultrasonic transducer coupled to a bottom of the sump and at least partially disposed within the sump; a vaporizing chamber fluidically coupled to the sump; and a heating element coupled to the vaporizing chamber and configured to increase a temperature of a surface disposed within the vaporizing chamber.

16 Claims, 5 Drawing Sheets

SYSTEMS AND METHODS FOR AN ULTRASONICALLY DRIVEN ANESTHETIC VAPORIZER

CROSS-REFERENCE TO RELATED APPLICATION(S)

This application is a divisional of U.S. patent application Ser. No. 16/184,678 filed on Nov. 8, 2018, in the U.S. Patent & Trademark Office, the disclosure of which is incorporated by reference herein in its entirety.

FIELD

Embodiments of the subject matter disclosed herein relate to anesthesia systems, and more particularly, to anesthetic vaporizers.

BACKGROUND

During some medical procedures, such as surgical procedures, a patient may be placed under general anesthesia by administrating an anesthetic agent. In some examples, the anesthetic agent may be a volatile anesthetic agent that is administered to the patient via an anesthetic vaporizer. For example, the anesthetic vaporizer may induce and control vaporization of the volatile anesthetic agent from a liquid form. A carrier gas (e.g., a mixture of oxygen and fresh air) may flow into the vaporizer and blend (e.g., mix and converge) with the anesthetic agent vapors generated by the vaporizer. An amount of carrier gas flowing into the vaporizer may be adjusted by an operator of the vaporizer (e.g., an anesthesiologist) in order to adjust a ratio of carrier gas to anesthetic agents within the vaporizer. Additionally, the output flow from the vaporizer can be adjusted via a proportional valve. The mixed gases may then flow to the patient, where they may be introduced via inhalation, for example.

BRIEF DESCRIPTION

In one embodiment, a system for an anesthesia vaporizer includes a sump configured to hold a liquid anesthetic agent; an ultrasonic transducer coupled to a bottom of the sump and at least partially disposed within the sump; a vaporizing chamber fluidically coupled to the sump; and a heating element coupled to the vaporizing chamber and configured to increase a temperature of a surface disposed within the vaporizing chamber. In this way, a low cost, compact anesthetic vaporizer is provided that may accurately deliver anesthetic agent to a patient with a fast response time.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1A:
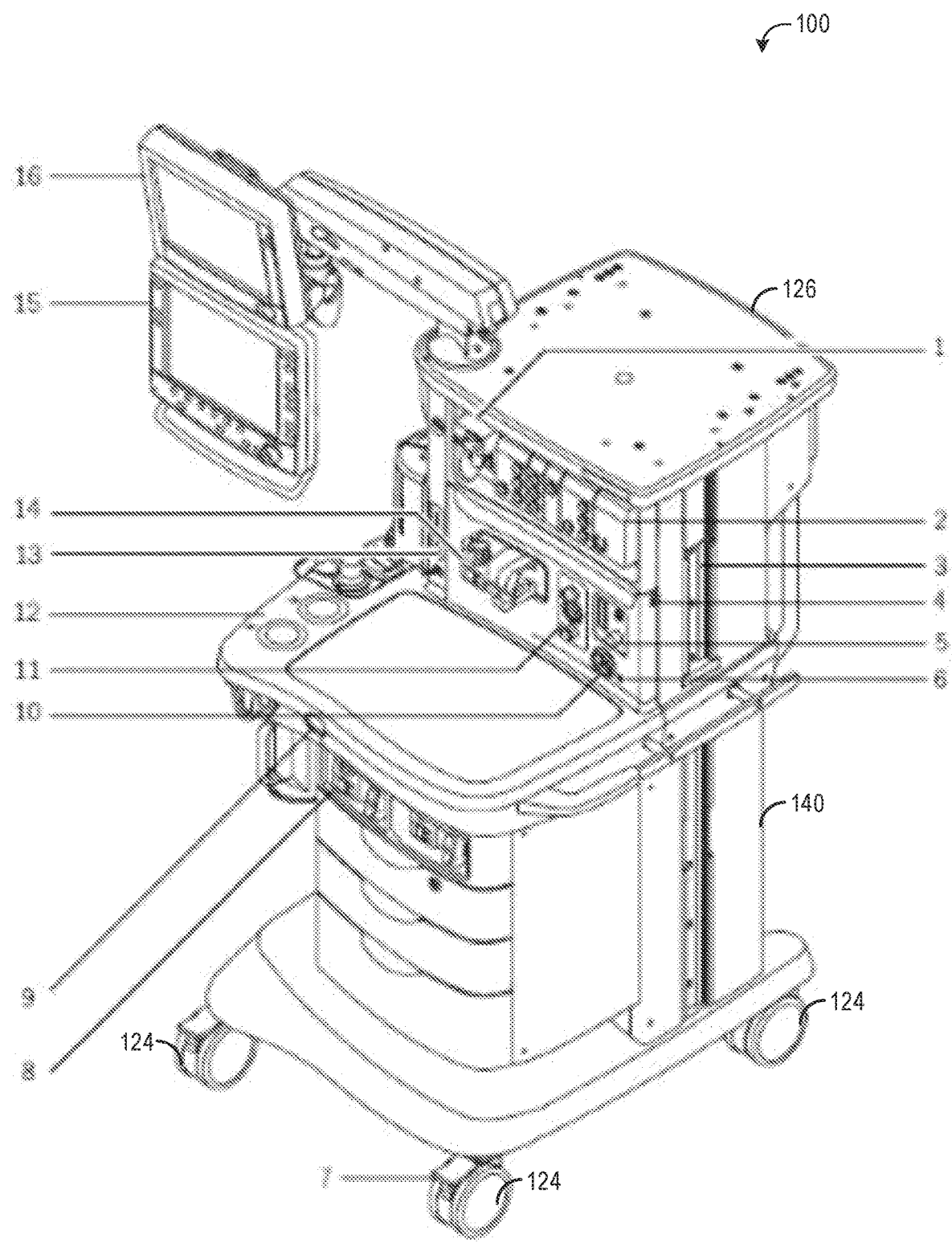
FIGS. 1A, 1B, and 1C show a first front perspective view, a second front perspective view, and back perspective view, respectively, of an exemplary anesthesia machine adapted to supply anesthetic agents to lungs of a patient.

The following description relates to various embodiments of an anesthetic vaporizer system, which may be included in an anesthesia system. Accurate, energy-efficient delivery of an anesthetic agent by a compact anesthetic vaporizer system may be challenging. For example, traditional anesthetic vaporizers systems may include pumps, compressors, pressurized sumps, pressurized secondary chambers, and/or injectors. As an example, a pump may deliver liquid anesthetic agent from a sump to a secondary chamber, where the liquid anesthetic agent is bulk boiled by a heater to vaporize the anesthetic agent and pressurize the secondary chamber. Including the pump, the sump, and the secondary chamber increases a size of the anesthetic vaporizer system and increases the cost of the anesthetic vaporizer system. Further, bulk boiling the liquid anesthetic agent increases an amount of energy consumed by the anesthetic vaporizer system due to a high thermal mass of the liquid anesthetic agent, which also creates a slow response to varying the amount of vaporized anesthetic agent produced through heater control.

Thus, according to embodiments disclosed herein, an ultrasonic transducer may be used to nebulize liquid anesthetic agent within a sump of an anesthetic vaporizer system and deliver the nebulized liquid anesthetic agent to a vaporizing chamber. Further, the vaporizing chamber may include a surface heated by an external heater, the heated surface providing heat energy for vaporizing the nebulized liquid anesthetic agent. By adjusting a gain to the ultrasonic transducer and/or an amount of power supplied to the heater, an amount of anesthetic agent vapor output by the anesthetic vaporizer system may be adjusted. Further, according to embodiments disclosed herein, the amount of anesthetic agent vapor output by the anesthetic vaporizer system may be controlled in a closed-loop fashion based on electronic feedback signals to accurately provide a desired amount of anesthesia to a patient.

The embodiments disclosed herein may provide several advantages. For example, the embodiments disclosed herein may provide a low cost and compact anesthetic vaporizer system through the use of an ultrasonic transducer to both transport and nebulize the liquid anesthetic agent. For example, the anesthetic agent delivery is simplified, without moving parts (e.g., such as a pump), fewer components, and a reduced amount of plumbing (e.g., by coupling the ultrasonic transducer in the sump). Further, by providing heat to the nebulized liquid anesthetic agent via the heater and the vaporizing chamber surface instead of bulk boiling the anesthetic agent, a quick response time may be achieved compared with bulk boiling due to a smaller thermal mass of the nebulized liquid anesthetic agent and the vaporizing chamber surface. For example, a heat transfer efficiency may be increased by heating the nebulized liquid anesthetic agent instead of the liquid anesthetic agent within the sump. Additionally, the sump may be refilled during anesthetic vaporizer system usage, as the sump is not pressurized.

Further still, the embodiments disclosed herein may provide additional advantages for controlling the amount of anesthetic agent vapor output by the anesthetic vaporizer system and delivered to the patient. For example, one or more of the ultrasonic transducer, the heater, and a flow control valve may be adjusted to adjust the amount of anesthetic agent vapor output by the anesthetic vaporizer system, providing control flexibility and allowing the amount of anesthetic agent vapor output by the anesthetic vaporizer system to be fine-tuned.

Figure 1B:
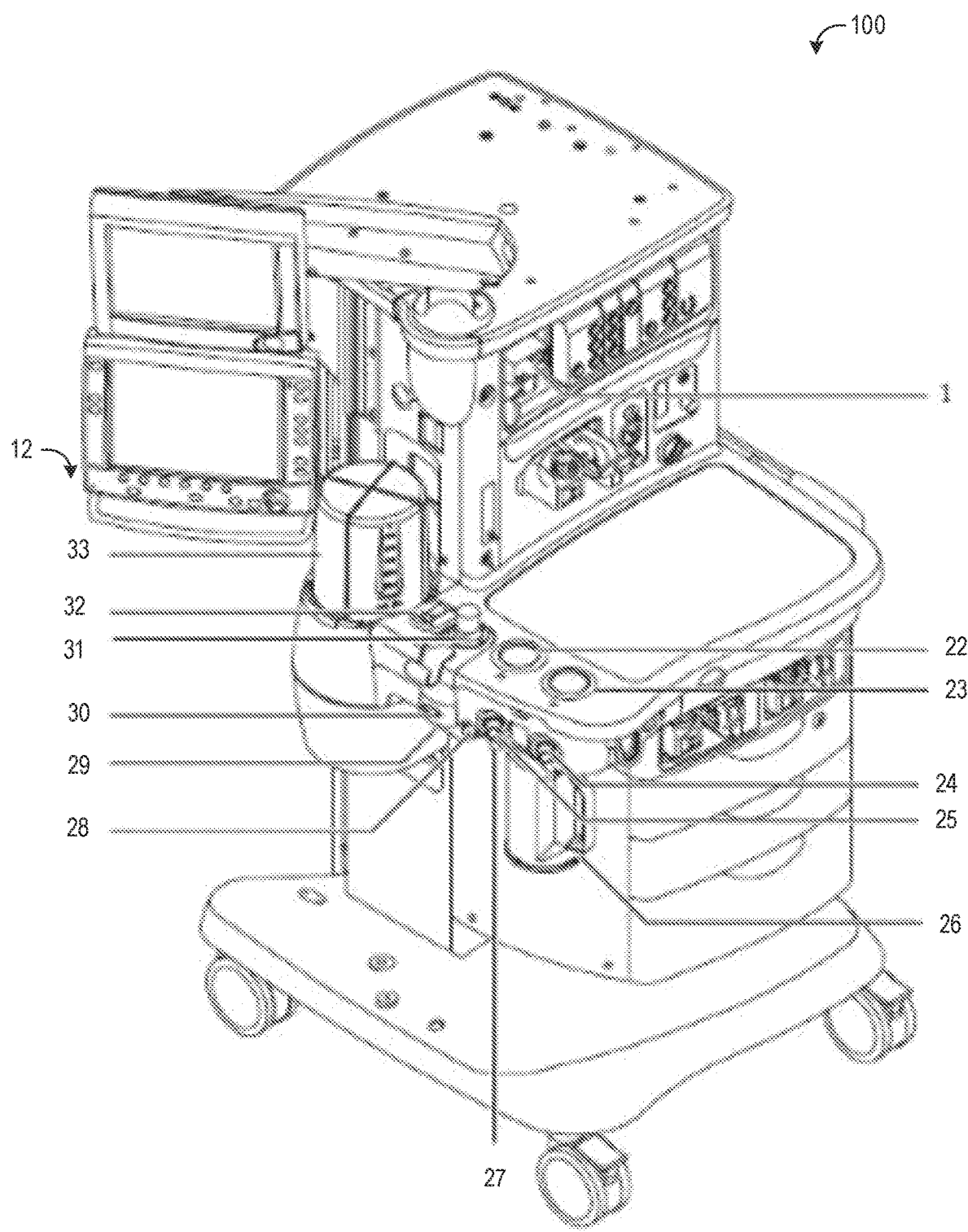
Figure 1C:
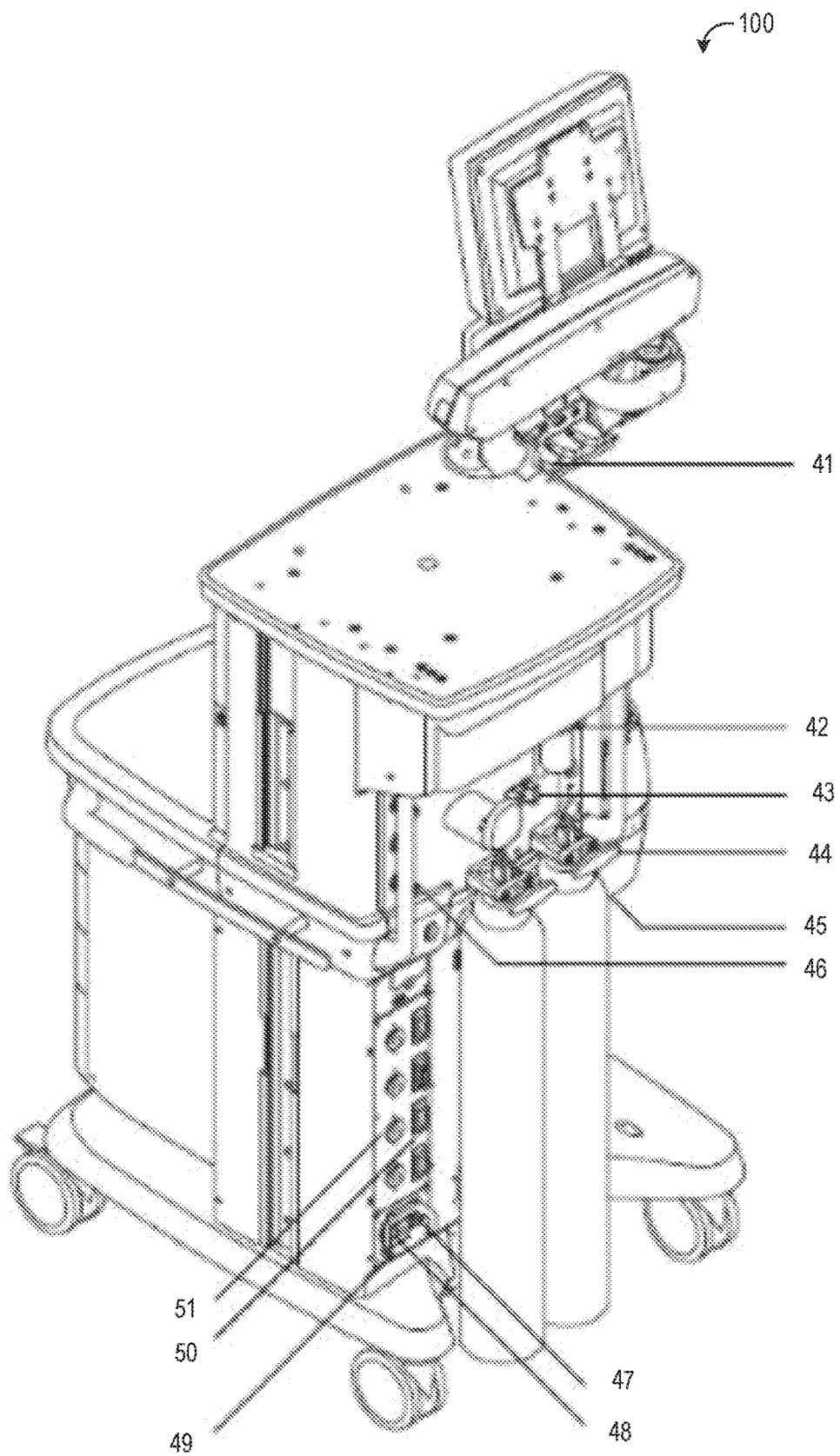
Figure 2:
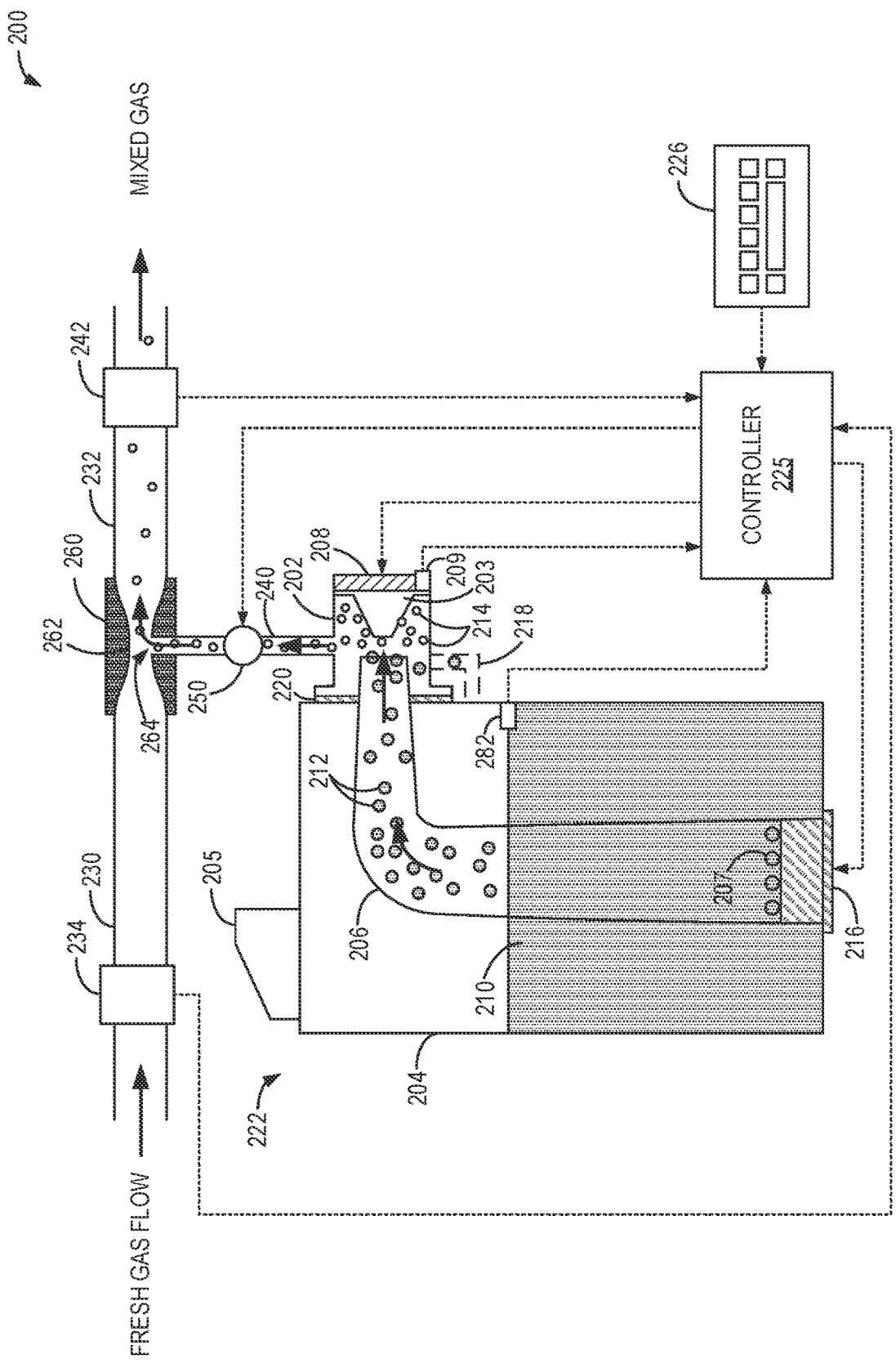
FIG. 2 schematically shows an example anesthetic vaporizer system including an ultrasonic transducer for nebulizing liquid anesthetic agent and a heating element for vaporizing the nebulized liquid anesthetic agent.

FIGS. 1A-1C show views of an example anesthesia machine according to an embodiment of the invention. FIG. 2 shows an example anesthetic vaporizer system, which may be included in the anesthesia machine of FIGS. 1A-1C. The anesthetic vaporizer system of FIG. 2 includes an ultrasonic transducer for both nebulizing and delivering anesthetic agent to a vaporizing chamber, where it may be supplied with energy for a phase change from liquid to vapor by a heating element. The amount of vapor produced by the anesthetic vaporizer system may be controlled using the example method of FIG. 3.

FIGS. 1A-1C show an anesthesia machine 100 from a first side perspective view (FIG. 1A), a second side perspective view (FIG. 1B), and rear perspective view (FIG. 1C). FIGS. 1A-1C will be described collectively. Anesthesia machine 100 includes a frame 126 supported by casters 124, where the movement of the casters may be controlled (e.g., stopped) by one or more locks 7. In some examples, the frame 126 may be formed of a plastic material (e.g., polypropylene). In other examples, the frame 126 may be formed of a different type of material (e.g., metal, such as steel).

Anesthesia machine 100 also includes a respiratory gas module 1, one or more patient monitoring modules, such as a patient monitoring module 2, side rails 3, a light switch 4, an oxygen control 5, a main power indicator 6, an anesthetic agent storage bay 8, an oxygen flush button 9, a system activation switch 10 (which, in one example, permits gas flow when activated), an integrated suction 11, a ventilator 12 (explained in more detail below), an auxiliary oxygen flow control 13, an anesthetic vaporizer 14, an anesthesia display device 15, and a patient monitoring display device 16. An example embodiment of the anesthetic vaporizer will be described below with respect to FIG. 2. The anesthetic vaporizer 14 may vaporize the anesthetic agent and combine the vaporized anesthetic agent with one or more medical grade gases (e.g., oxygen, air, nitrous oxide, or combinations thereof), which may then be delivered to a patient.

A rear of the anesthesia machine 100 is shown in FIG. 1C. On the rear of the anesthesia machine, one or more pipeline connections 46 are present to facilitate coupling of the anesthesia machine to pipeline gas sources. Additionally, the rear of the anesthesia machine includes a cylinder yoke 44, via which one or more gas-holding cylinders may be coupled to the anesthesia machine. Thus, through the pipeline connection and/or cylinder connections, gas may be provided to the anesthesia machine, where the gas may include but is not limited to air, oxygen, and nitrous oxide. The gas that enters the anesthesia machine may mix with the vaporized anesthetic agent at the anesthetic vaporizer 14, as described above, and be supplied to a patient via the ventilator 12. The rear of the anesthesia machine may also include a serial port 41, a collection bottle connection 42, a cylinder wrench storage area 43, an anesthesia gas scavenging system 45, a main power inlet 47, a system circuit breaker 48, an equipotential stud 49, an outlet circuit breaker 50, and an isolated electrical outlet 51.

As shown in FIG. 1B, the ventilator 12 may include an expiratory check valve 22 at an expiratory port, an inspiratory check valve 23 at an inspiratory port, an inspiratory flow sensor 24, an expiratory flow sensor 25, an absorber canister 26, an absorber canister release 27, a leak test plug 28, a manual bag port 29, a ventilator release 30, an adjustable pressure-limiting valve 31, a bag/vent switch 32, and a bellows assembly 33. When a patient breathing circuit is coupled to the ventilator 12, breathing gases (e.g., air, oxygen, and/or nitrous oxide mixed with vaporized anesthetic agent) exit the machine from the inspiratory port (positioned at the same location as the inspiratory check valve 23) and travel to the patient. Expiratory gases from the patient re-enter the anesthesia machine via the expiratory port (positioned at the same location as the expiratory check valve 22), where carbon dioxide may be removed from the expiratory gases via the absorber canister 26.

During operation of the anesthetic vaporizer 14, an operator (e.g., an anesthesiologist) may adjust an amount of vaporized anesthetic agent that is supplied to the patient by adjusting a flow rate of gases from the gas source(s) (e.g., the gas pipelines) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of the anesthesia machine 100. In one example, a first flow control valve may be positioned between the gas source(s) and the anesthetic vaporizer 14 and may be actuatable via the flow adjustment devices to a fully opened position, a fully closed position, and a plurality of positions between the fully opened position and the fully closed position. Different flow control valves that may be adjusted to vary an amount of vaporized anesthetic agent that is supplied to the patient will be further described below with respect to FIG. 2.

The anesthesia machine may additionally include one or more valves configured to bypass gases from the gas source (s) around the anesthetic vaporizer 14. The valves may enable a first portion of gases to flow directly from the gas source to the inspiratory port and a second portion of gases to flow from the gas source through the anesthetic vaporizer 14 to mix with the vaporized anesthetic agents prior to flowing to the inspiratory port. By adjusting a ratio of the first portion of gases relative to the second portion of gases, the operator may control a concentration of vaporized anesthetic agent administered to the patient via the inspiratory port.

Further, the adjustments described above may be facilitated at least in part based on output from the respiratory gas module 1. The respiratory gas module 1 may be configured to measure various parameters of the gases exiting the vaporizer and/or being provided to the patient. For example, respiratory gas module 1 may measure the concentrations of carbon dioxide, nitrous oxide, and the anesthetic agent provided to the patient. Further, respiratory gas module 1 may measure respiration rate, minimum alveolar concentration, patient oxygen, and/or other parameters. The output from the respiratory gas module 1 may be displayed via a graphical user interface on a display device (e.g., anesthesia display device 15 and/or patient monitoring display device 16) and/or used by a controller to provide closed-loop feedback control of the amount of anesthesia provided to the patient.

Ventilator 12 may optionally be coupled to a breathing circuit (not shown) including a plurality of tubes (e.g., gas passages). The breathing circuit may be coupled between an airway of a patient (e.g., via a breathing mask positioned to enclose the mouth and/or nose of the patient or a tracheal intubation tube) and the inspiratory port. Gases (e.g., oxygen, or a mixture of oxygen and vaporized anesthetic agents from anesthetic vaporizer 14) may flow from the inspiratory port, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gases (without the anesthetic agent) may flow into the airway of the patent (e.g., through inhalation) via the inspiratory check valve 23. As an example, the inspiratory check valve 23 may open automatically (e.g., without input or adjustment by the operator) in response to inhalation by the patient and may close automatically in response to exhalation by the patient. Similarly, the expiratory check valve 22 may open automatically in response to exhalation by the patient and may close automatically in response to inhalation by the patient.

In some examples, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 14, the ventilator 12, the respiratory gas module 1, the anesthesia display device 15, and the patient monitoring display device 16.

The controller receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port may be controlled via an input device (e.g., keyboard, touchscreen, etc.) coupled to the electronic controller of the anesthesia machine 100. The controller 140 may display operating parameters of the anesthesia machine 100 via anesthesia display device 15 and/or patient monitoring display device 16. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by inspiratory flow sensor 24, for example.

Controller 140 is shown in FIG. 1A for illustrative purposes, and it is to be understood that controller 140 may be located internally of anesthesia machine 100 and thus may not be visible externally on anesthesia machine 100. Additionally, controller 140 may include multiple devices/modules that may be distributed throughout anesthesia machine 100. As such, controller 140 may include a plurality of controllers at various locations within anesthesia machine 100 and/or external to anesthesia machine 100 that are communicatively coupled through wired and/or wireless connections.

Anesthetic vaporizers, such as anesthetic vaporizer 14 shown in FIG. 1A, may employ various methods to vaporize a liquid anesthetic agent. For example, a traditional anesthetic vaporizer may include a wick that is saturated with the liquid anesthetic agent, and a stream of medical grade gas from a fresh gas flow (e.g., air, oxygen, nitrous oxides, or a combination thereof) is flowed past the wick to pull vapor from the liquid anesthetic agent into the stream. The fresh gas flow is split into carrier gas, which flows past the wick, and bypass gas, which does not flow past the wick, and thus the amount of the anesthetic agent liberated from the wick is determined by the amount of gas flowed past the wick (e.g., the carrier gas) and wick surface area. Other vaporization techniques have included heating the liquid anesthetic agent within a sump or secondary vessel to generate vapor, and a proportional valve is used to control flow of the vapor into the gas stream. However, this comes at a penalty of either pressurizing sump, which requires depressurizing to fill, or using a pump to move liquid to secondary chamber for vaporizing. Further, systems based on pressurized liquid agent combined with automotive style "fuel" injectors have been used, but utilize a pump to provide pressurized liquid anesthetic agent to the injectors. Furthermore, the injectors may be sensitive to particles in the anesthetic agent, such as by becoming partially or fully clogged.

FIG. 2 schematically shows an example embodiment of an anesthetic vaporizer system 200, which may be included in an anesthesia system (e.g., anesthesia system 100 shown in FIGS. 1A-1C). As one example, anesthetic vaporizer system 200 may be anesthetic vaporizer 14 of FIG. 1A. In particular, anesthetic vaporizer system 200 utilizes ultrasonic energy imparted by an ultrasonic transducer 216 to nebulize a liquid anesthetic agent 210 that is stored within a sump 222. Sump 222 includes a housing 204 and a refilling port 205. For example, the liquid anesthetic agent 210 stored within sump 222 may be replenished via refilling port 205. In some examples, refilling port 205 may include a bottle adapter and a valve, the valve held in a closed position by a spring. The spring may be compressed by threading a bottle of the liquid anesthetic agent onto the bottle adapter, resulting in opening of the valve. Upon opening of the valve, the liquid anesthetic agent may flow to into sump 222 without spillage.

Ultrasonic transducer 216 is coupled to a bottom surface of housing 204 and extends into a bottom opening of a mist transfer tube 206 disposed within sump 222. For example, the bottom opening of mist transfer tube 206 may form a fluid-tight seal with housing 204, and ultrasonic transducer 216 may form a fluid-tight seal with both mist transfer tube 206 and housing 204. Ultrasonic transducer 216 may include a single transducer element or multiple transducer elements. The transducer element(s) generates acoustic signals (e.g., in the ultrasonic range, which may be above 18 kHz) in response to electrical signals (e.g., voltage signals) output by a pulser of the ultrasonic transducer 216, for example. The transducer element(s) may comprise a piezoelectric element or a capacitive element. Ultrasonic transducer 216 may be activated to provide vaporized anesthetic agent to a patient responsive to a control signal from a controller 225, as will be further described below. Controller 225 may be an electronic controller including a processor operatively connected to a memory. Controller 225 may be included in (e.g., a part of) or communicatively coupled to controller 140 shown in FIG. 1A, for example.

Further, data may be input to controller 225 by an operator of anesthetic vaporizer system 200 (e.g., an anesthesiologist) via a user input device 226 that is operationally connected to the controller and thus configured to transmit an input signal to controller 225 (e.g., via wired or wireless communication). User input device 226 may include one or more of a mouse, a keyboard, a voice input device, a touch input device for receiving a gesture from the operator, a motion input device for detecting non-touch gestures and other motions by the operator, and other comparable input devices, as well as associated processing elements capable of receiving user input from the operator.

A plurality of openings 207 in mist transfer tube 206 near or partially overlapping with a position of ultrasonic transducer 216 may enable liquid anesthetic agent 210 to enter into mist transfer tube 206. The plurality of openings 207 may be circular, as shown, elliptical, or any other appropriate geometry. When ultrasonic transducer 216 is activated, kinetic energy imparted by the ultrasonic transducer causes liquid anesthetic agent 210 move at a high velocity, causing liquid anesthetic agent 210 to break up into a plurality of mist droplets 212 at a surface of the liquid. Further, the kinetic energy imparted by ultrasonic transducer 216 causes the plurality of mist droplets 212 to travel up mist transfer tube 206. An amount of liquid anesthetic agent 210 nebulized by ultrasonic transducer 216 into mist droplets 212 may be controlled by adjusting a frequency or drive amplitude of ultrasonic transducer 216. Additionally or alternatively, the amount of liquid anesthetic agent 210 nebulized by ultrasonic transducer 216 may be controlled via pulse-width modulation (PWM) of ultrasonic transducer 216. As an example, controller 225 may receive a target amount of anesthetic agent to deliver to a patient (e.g., via input from the operator). In response, controller 225 may determine a frequency, drive amplitude, and/or duty cycle of ultrasonic transducer 216 activation based on the input target amount of anesthetic agent and send a corresponding control signal to ultrasonic transducer 216, as will be further described below with respect to FIG. 3.

Mist transfer tube 206 may direct the mist droplets 212 produced through ultrasonic transducer 216 activation to a vaporizing chamber 202. For example, as shown in FIG. 2, mist transfer tube 206 may curve so that a top opening of the mist transfer tube is substantially perpendicular to the bottom opening of the mist transfer tube. Further, at least in some examples, mist transfer tube 206 may be tapered such that the diameter of mist transfer tube 206 gradually decreases from the bottom opening to the top opening. The top opening of mist transfer tube 206 may extend beyond housing 204 of sump 222 and into vaporizing chamber 202, which may be coupled to housing 204 with a thermal insulator 220 positioned therebetween. A heating element 208 coupled to vaporizing chamber 202 may be configured to heat vaporizing chamber 202, such as by heating a surface 203 that extends within vaporizing chamber 202. Heating element 208 may heat through conduction, for example. As one example, heating element 208 may be a resistive heating element that increases in temperature as a current or voltage supplied to the heating element increases. Therefore, controller 225 may regulate an amount of current or voltage supplied to heating element 208 in order to control a temperature of heating element 208 (and/or surface 203), as will be further described below with respect to FIG. 3. Thermal insulator 220 may reduce heat transfer from vaporizing chamber 202 to sump 222, thereby reducing or preventing pressurization of sump 222 that would result from heating liquid anesthetic agent 210. For example, thermal insulator 220 may be comprised of a relatively high heat capacity, relatively low thermal conductivity material.

Upon exiting mist transfer tube 206 and entering vaporizing chamber 202, the mist droplets 212 may impinge on the heated surface 203, causing the liquid anesthetic agent to undergo a phase change to form anesthetic agent vapor 214. Surface 203 may be generally conical in shape, as shown in FIG. 2, although other geometries are also possible. As used herein, "generally conical" includes shapes having side surfaces that taper from a wider base (which is more proximal to heating element 208 in FIG. 2) to a narrower vertex (which is more proximal to mist transfer tube 206 in FIG. 2). A pyramid, which has a polygonal base, is generally conical, for example. Further, "generally conical" includes shapes that have a plane as the vertex, as shown in FIG. 2, or a point as the vertex. The geometry of surface 203 may be selected to increase a surface area of surface 203 as well as facilitate impingement of the mist droplets 212 onto surface 203. Furthermore, surface 203 may be textured, such as ribbed, to further increase the surface area of surface 203. Surface 203 may be comprised of metal or another appropriate material with a relatively low specific heat capacity, a relatively high thermal conductivity, and a relatively high temperature durability so that operation of heating element 208 may efficiently increase a temperature of surface 203 without warping or degrading surface 203.

As another example, heating element 208 may be an inductive heating element that selectively increases a temperature of surface 203, and surface 203 may comprise a metal grid, such as a metal mesh. In such an example, surface 203 may be positioned such that the mist droplets 212 contact the metal grid upon exiting mist transfer tube 206 and entering vaporizing chamber 202. By including heating element 208 as an inductive heating element and surface 203 as a metal grid, a greater proportion of the mist droplets 212 may contact the heated surface 203 compared with when heating element 208 heats through conduction and surface 203 is not a metal grid. Further, a warm up time (e.g., an amount of time before surface 203 reaches a desired temperature after activating heating element 208) may be substantially reduced via use of induction heating compared to conventional conduction heating.

Anesthetic vaporizer system 200 optionally includes a liquid return line 218 that couples vaporizing chamber 202 to sump 222, such as via an opening in housing 204. Liquid return line 218 may form a gas-tight seal with both vaporizing chamber 202 and housing 204. The optional liquid return line 218 enables mist droplets 212 that are not converted to anesthetic agent vapor 214 within vaporizing chamber 202 to return to sump 222, for example, if an excess amount of liquid anesthetic agent 210 is nebulized by ultrasonic transducer 216. In some examples, controller 225 may adjust one or more or each of ultrasonic transducer 216 operation and heating element 208 operation to fine-tune an amount of liquid anesthetic agent 210 that is converted to anesthetic agent vapor 214, as will be further described below with respect to FIG. 3.

The anesthetic agent vapor 214 may exit vaporizing chamber 202 via a vapor delivery passage 240 and flow to a venturi 260. An inlet of venturi 260 is coupled to a gas inlet passage 230, through which fresh gas flow is provided to venturi 260, and an outlet of venturi 260 is coupled to a gas outlet passage 232. The fresh gas flow may include one or more medical gases, such as oxygen, air, nitrous oxide, and combinations thereof. The fresh gas flow may be provided via one or more gas pipelines (e.g., via pipeline connections 46 shown in FIG. 1C) and/or one or more gas-holding cylinders (e.g., via cylinder yoke 44 of FIG. 1C). Venturi 260 includes a tapered tube 262. As shown in FIG. 2, a diameter of tapered tube 262 may match that of gas inlet passage 230 where tapered tube 262 and gas inlet passage 230 are joined. The diameter of tapered tube 262 may gradually decrease until a minimum diameter is reached. For example, the minimum diameter may be maintained throughout a throat region 264 before gradually increasing again to match that of gas outlet passage 232 where tapered tube 262 and gas outlet passage 232 are joined. The diameter of gas inlet passage 230 (and the inlet of venturi 260) may be the same as the diameter of gas outlet passage 232 (and the outlet of venturi 260), at least in some examples. Vapor delivery passage 240, which has a smaller diameter than each of gas inlet passage 230 and gas outlet passage 232, is shown coupled to tapered tube 262 of venturi 260 at throat region 264. As the fresh gas flows through tapered tube 262, a pressure drop occurs at throat region 264 that pulls the anesthetic agent vapor 214 into the fresh gas stream, resulting in mixed gas containing both the fresh gas from the fresh gas flow and the anesthetic agent vapor 214. For example, the mixed gas may be a homogenous mixture of the fresh gas and the anesthetic agent vapor 214.

A mass flow sensor 234 is shown coupled to gas inlet passage 230. Mass flow sensor 234 may transmit a signal to controller 225 indicative of a mass flow rate of the fresh gas within gas inlet passage 230 (e.g., upstream of venturi 260). The mass flow rate of the fresh gas may be used by controller 225 in part to determine an amount of power to supply to ultrasonic transducer 216, as will be further described below with respect to FIG. 3.

A concentration sensor 242 is positioned in gas outlet passage 232. Concentration sensor 242 may be any suitable sensor that is configured to measure a concentration of the anesthetic agent in the mixed gas. In one example, concentration sensor 242 may be an optical sensor that transmits light of a suitable wavelength (e.g., infrared) through the mixed gas and determines a concentration of the anesthetic agent based on an absorption of the light by the mixed gas. Concentration sensor 242 may output a signal to controller 225 indicative of the measured concentration of the anesthetic agent (e.g., the concentration of the anesthetic agent vapor 214) in the mixed gas.

After flowing through concentration sensor 242, the mixed gas may be delivered to the patient via an inspiratory limb of a breathing circuit (e.g., via the inspiratory port described with respect to FIG. 1B). For example, gas outlet passage 232 may be coupled to a mask, tracheal tube, or other suitable breathing circuit component, either proximally or distally.

A valve 250 may be coupled between vaporizing chamber 202 and throat region 264 of venturi 260. In the example shown in FIG. 2, valve 250 is coupled to vapor delivery passage 240, however, in other examples, valve 250 may be included in venturi 260. In one example, valve 250 may be an on-off valve, such as a shut-off valve, where valve 250 is actuated between an "open" (e.g., fully open) position that allows vaporized anesthetic agent 214 to flow between vaporizing chamber 202 and throat region 264 and a "closed" (e.g., fully closed) position that prevents (e.g., blocks) the flow of vaporized anesthetic agent 214 between vaporizing chamber 202 and neck region 264. Valve 250 may be actuated between the open and closed positions in response to an appropriate command signal from controller 225, for example. As another example, valve 250 may be a variable valve, such as a proportional valve, that may be actuated to a plurality of positions between fully open and fully closed based on the command signal from controller 225. For example, controller 225 may adjust the position of valve 250 based on the target amount of anesthetic agent to deliver to the patient, with a degree of opening of valve 250 increasing as the target amount of anesthetic agent increases, as will be further described below with respect to FIG. 3. Whether valve 250 is a shut-off valve or a proportional valve, as one example, valve 250 may be actuated to the fully closed position by controller 225 in response to input from the operator (e.g., via input device 226) to stop the supply of the anesthetic agent to the patient.

In addition to receiving signals output by mass flow sensor 234 and concentration sensor 242, controller 225 may receive additional signals, including a temperature of heating element 208 from a temperature sensor 209 coupled to heating element 208 (or coupled to surface 203) and a measured fluid level (e.g., of liquid anesthetic agent 210) from a fluid level sensor 282. For example, fluid level sensor 282 may be a float type sensor, a radar level transmitter, an ultrasonic level transmitter, a magnetic level gauge, a differential pressure level sensor, or any other suitable sensor configured to measure the level of liquid anesthetic agent 210 and output the measured level to controller 225. Controller 225 receives the signals from the various sensors of FIG. 2, processes the input data, and employs the various actuators of FIG. 2 to adjust operation of the anesthetic vaporizer system 200 based on the received signals and instructions stored on a memory of the controller. For example, controller 225 may receive the measured mass flow rate from mass flow sensor 234 and the measured concentration of the anesthetic agent from concentration sensor 242 and adjust a control signal transmitted to one or more of ultrasonic transducer 216, heating element 208, and valve 250 in response, as will be further described below with respect to FIG. 3.

Thus, anesthetic vaporizer system 200 provides a system for delivering liquid anesthetic agent to a patient in vaporized form without use of a pump or pressurization. By using an ultrasonic transducer to provide a fine mist of liquid anesthetic agent to a heated surface of a vaporizing chamber, heat transfer efficiency may be increased, thus reducing power input to a heating element and reducing a heat-up time. Furthermore, using an ultrasonic transducer for agent delivery may decrease a cost of the anesthetic vaporizer system while increasing a compactness of the system, as the delivery system is built inside of the sump (instead of providing liquid from the sump to a secondary chamber). Further still, the sump may be refilled during use because the sump is not pressurized. Additionally, due to the low cost of the ultrasonic transducer, in some examples, the anesthetic vaporizer system may be a single use, disposable module.

Figure 3:
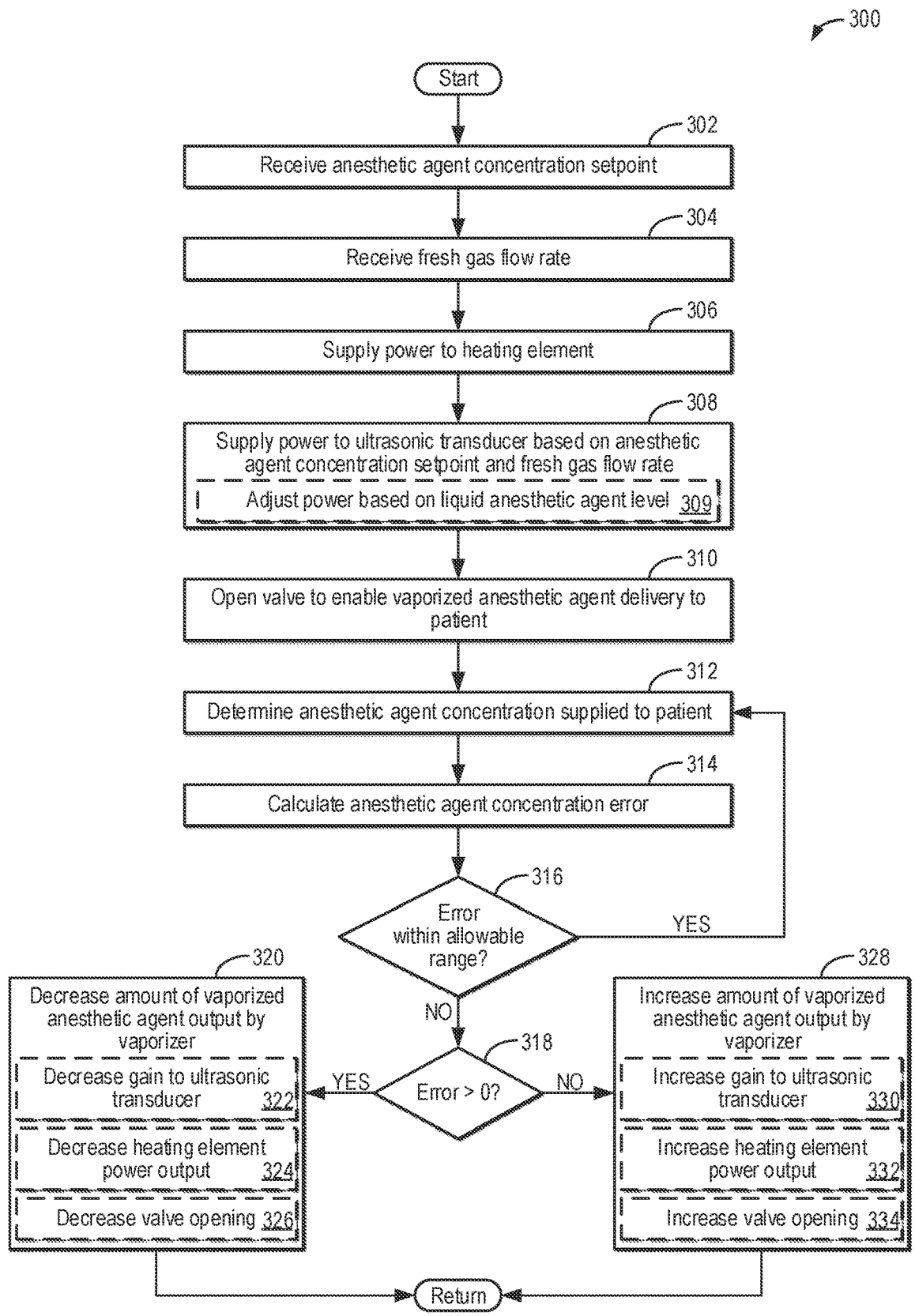
FIG. 3 is a flow chart illustrating an example method for controlling an amount of vaporized anesthetic agent delivered to a patient via the anesthetic vaporizer system of FIG. 2.

Turning now to FIG. 3, a method 300 for operating an anesthetic vaporizer system that includes an ultrasonic transducer for nebulizing a liquid anesthetic agent, such as anesthetic vaporizer system 200 of FIG. 2, is shown. For example, the anesthetic vaporizer system may be included in an anesthesia machine, such as anesthesia machine 100 of FIGS. 1A-1C. Method 300 may be carried out by a controller, such as controller 225 of FIG. 2, according to instructions stored in a memory of a controller and in conjunction with one or more sensors (e.g., mass flow sensor 234, fluid level sensor 282, temperature sensor 209, and concentration sensor 242 shown in FIG. 2) and actuators (e.g., heating element 208, valve 250, and ultrasonic transducer 216 of FIG. 2). For example, electrical power may be supplied to the ultrasonic transducer to nebulize a liquid anesthetic agent, and electrical power may be supplied to a heating element to heat a surface of a vaporizing chamber (e.g., surface 203 of vaporizing chamber 202 shown in FIG. 2) to a desired temperature for vaporizing the nebulized liquid anesthetic agent. The power supplied to each of the ultrasonic transducer and the heating element may be selected to provide a desired amount of anesthetic agent to a patient and may be further adjusted based on a measured amount of the anesthetic agent.

Method 300 begins at 302 and includes receiving an anesthetic agent concentration setpoint. The anesthetic agent may be any suitable volatile liquid anesthetic agent, such as desflurane, isoflurane, sevoflurane, or the like, or another medication that may be nebulized/inhaled, such as albuterol. The concentration setpoint may be a percentage of the vaporized anesthetic agent per volume of a fresh gas/vaporized anesthetic agent mix provided to a patient. The concentration setpoint, referring to the desired concentration of anesthetic agent to deliver to the patient, may be obtained via user input to the controller (e.g., via an input device 226) or via another suitable mechanism.

At 304, method 300 includes receiving a fresh gas flow rate. The fresh gas flow rate is a rate of fresh gas entering the anesthetic vaporizer system. For example, the mass flow sensor may measure the fresh gas flow rate and output a corresponding signal to the controller. In other examples, the fresh gas flow rate may be input to the controller via the user or by an additional controller communicatively coupled to the controller of the anesthetic vaporizer system (e.g., controller 140 of FIG. 1A).

At 306, method 300 includes supplying power to the heating element. For example, an amount of current or voltage supplied to the heating element may be regulated to achieve and/or maintain a desired operating temperature of the heating element and/or a heating target of the heating element (e.g., surface 203 shown in FIG. 2). The desired operating temperature may be selected (e.g., by the controller) based on the anesthetic agent concentration setpoint, for example. As an example, the controller may input the anesthetic agent concentration setpoint into a look-up table stored in a memory of the controller, and the look-up table may output the desired operating temperature for the input anesthetic agent concentration setpoint. As another example, the desired operating temperature may be a default temperature that is independent of the anesthetic agent concentration setpoint. For example, the default temperature may be specific to the anesthetic agent used, which may be input by the user or via another suitable mechanism. As such, the default temperature may be lower for a first anesthetic agent (e.g., with a lower boiling point) and higher for a second anesthetic agent (e.g., with a higher boiling point). The controller may input the anesthetic agent used into a look-up table stored in a memory of the controller, and the look-up table may output the default temperature corresponding to the input anesthetic agent, for example. As still another example, the default temperature may be independent of both of the anesthetic agent concentration setpoint and the identity of the anesthetic agent. The controller may input the desired operating temperature into one or more look-up tables, maps, or functions and may receive output of an amount of voltage to supply to the heating element (e.g., from a power source) and/or a duty cycle of voltage to supply to the heating element that will result in the desired operating temperature, for example. Further, in some examples, the controller may receive feedback regarding a measured temperature of the heating element (or the heated surface) from the temperature sensor and may adjust the amount and/or duty cycle of voltage suppled to the heating element based on the measured temperature. In some examples, the desired operating temperature, and thus the heater power output, may be selected such that substantially all of the nebulized anesthetic agent is vaporized upon contact with the heated surface. In other examples, the desired operating temperature may be selected such that the nebulized anesthetic agent is vaporized gradually over time.

At 308, method 300 includes supplying power to the ultrasonic transducer based on the anesthetic agent concentration setpoint and the fresh gas flow rate. For example, the controller may determine one or more of a frequency, a drive amplitude, and a duty cycle of the ultrasonic transducer based on the anesthetic agent concentration setpoint and the fresh gas flow rate. The controller may input the anesthetic agent concentration setpoint and the fresh gas flow rate into one or more look-up tables, functions, or algorithms stored in memory, which may then output one or more of the frequency, drive amplitude, and duty cycle of the ultrasonic transducer. As an example, as the anesthetic agent concentration setpoint and/or the fresh gas flow rate increases, the duty cycle of the ultrasonic transducer may increase. In some examples, the controller may further account for the heater power output (e.g., as determined at 306) when determining the frequency, drive amplitude, and/or duty cycle of the ultrasonic transducer. For example, when the selected heater power output is such that vaporization of the nebulized anesthetic agent provided by the ultrasonic transducer occurs over time, the ultrasonic transducer may be controlled via pulse-width modulation, with vaporization persisting during "off" periods of the ultrasonic transducer (e.g., when voltage is not supplied) due to the gradual vaporization by the heated surface. As a further example, a rate of nebulization of the liquid anesthetic agent by the ultrasonic transducer may be controlled via pulse-width modulation (PWM) of the transducer to provide a time averaged variable output. Additionally, adjusting of the drive frequency and transducer amplitude may be used alone or in combination, including in combination with PWM, to provide a wider dynamic range of nebulization output.

Further, as indicated at 309, supplying power to the ultrasonic transducer optionally further includes adjusting the power based on a level of the liquid anesthetic agent in the anesthetic vaporizer system (e.g., in sump 222 of FIG. 2), such as measured by the fluid level sensor. As an example, as the level of the liquid anesthetic agent decreases, an amount of kinetic energy for nebulizing the liquid anesthetic agent and propelling it up a mist transfer tube (e.g., mist transfer tube 206 of FIG. 2) to the vaporizing chamber may increase. Thus, in some examples, the controller may proactively adjust the frequency, drive amplitude, and/or duty cycle of the ultrasonic transducer operation to maintain the anesthetic agent concentration setpoint as the liquid anesthetic agent level changes. As an example, the controller may input the anesthetic agent concentration setpoint, the fresh gas flow rate, and the measured liquid anesthetic agent level into one or more look-up tables, functions, or algorithms, which may then output the frequency, drive amplitude, and/or duty cycle of the ultrasonic transducer operation. As another example, the controller may input a measured change in the liquid anesthetic agent level into one or more look-up tables, functions, or models, which may then output an adjustment to be made to one or more of the frequency, drive amplitude, and duty cycle of the ultrasonic transducer operation to compensate for the input change in the liquid anesthetic agent level. However, in other examples, the controller may not proactively adjust the frequency, drive amplitude, and/or duty cycle of the ultrasonic transducer operation based on the measured liquid anesthetic agent level.

At 310, method 300 includes opening a valve to enable vaporized anesthetic agent delivery to the patient. For example, the valve may be a shut-off valve (e.g., valve 250 of FIG. 2) that, when open, allows the vaporized anesthetic agent to flow out of the vaporizing chamber and join the fresh gas flow, resulting in mixed gas comprising the vaporized anesthetic agent and the fresh gas. The mixed gas may then flow from the anesthetic vaporizer to the patient, such as via an inspiratory limb of a breathing circuit. Therefore, the controller may send a command signal to the valve to actuate the valve to the open (e.g., fully open) position. As another example, if the valve is already open, the valve may be maintained in the open position. As still another example, when the valve is a proportional valve, the controller may actuate the valve to a desired open position (e.g., a desired degree of opening), the desired open position determined based on the anesthetic agent concentration setpoint and the fresh gas flow rate. For example, the controller may input the anesthetic agent concentration setpoint and the fresh gas flow rate into one or more look-up tables, functions, or algorithms stored in memory, which may then output the corresponding open position. As an example, as the anesthetic agent concentration setpoint increases, the degree of opening of the valve may increase.

At 312, method 300 includes determining a concentration of the anesthetic agent supplied to the patient. For example, the concentration of the anesthetic agent supplied to the patient (e.g., via the anesthesia machine) may be measured by the concentration sensor, which may be positioned in a gas outlet passage of the anesthetic vaporizer system (e.g., gas outlet passage 232 shown in FIG. 2). The concentration sensor may output a signal corresponding to the measured concentration of the anesthetic agent to the controller. Further, the output signal may be time averaged to filter out small time variability in the measured concentration because a long length of the anesthesia machine enables further gas mixing such that variation at the gas outlet passage of the anesthetic vaporizer system is effectively negated at the patient input.

At 314, method 300 includes calculating an anesthetic agent concentration error. The anesthetic agent concentration error may be the difference between the setpoint agent concentration and the measured agent concentration. For example, the anesthetic agent concentration error (ERR) may be calculated as:

$$ERR = Agent_{actual} - Agent_{setpoint}$$

where $Agent_{actual}$ is the concentration of the anesthetic agent supplied to the patient (e.g., as determined at 312) and $Agent_{setpoint}$ is the anesthetic agent concentration setpoint (e.g., as received at 302).

At 316, method 300 includes determining if the anesthetic agent concentration error is within an allowable range. As an example, the allowable range may be defined by a lower threshold value and an upper threshold value. In some examples, the lower threshold value may be an anesthetic agent concentration error value that corresponds to an anesthetic agent concentration value that is a percentage below the anesthetic agent concentration setpoint, and the upper threshold value may be an anesthetic agent concentration error value that corresponds to an anesthetic agent concentration value that is the percentage above the anesthetic agent concentration setpoint. Thus, the allowable range may encompass anesthetic agent concentration error values for the concentration of the anesthetic agent supplied to the patient remaining within the percentage of the anesthetic agent concentration setpoint. In some examples, the percentage may vary based on one or more of the anesthetic agent concentration setpoint and the anesthetic agent used, such that the percentage may be smaller when the anesthetic used is more precisely controlled.

If the anesthetic agent concentration error is within the allowable range, method 300 returns to 312 and includes continuing to determine the concentration of the anesthetic agent supplied to the patient. In this way, the anesthetic agent concentration error may be updated as the anesthetic agent concentration supplied to the patient changes. If the anesthetic agent concentration error is not within the allowable range, method 300 proceeds to 318 and includes determining if the error is greater than zero. For example, when the anesthetic agent concentration error is greater than zero (e.g., greater than the upper threshold value), the anesthetic agent concentration delivered to the patient is greater than the anesthetic agent concentration setpoint (e.g., greater than the percentage above the anesthetic agent concentration setpoint). When the anesthetic agent concentration error value is not greater than zero (e.g., is less that the lower threshold value), the anesthetic agent concentration delivered to the patient is less than the anesthetic agent concentration setpoint (e.g., less than the percentage below the anesthetic agent concentration setpoint).

If the anesthetic agent concentration error is greater than zero, method 300 proceeds to 320 and includes decreasing the amount of vaporized anesthetic agent output by the vaporizer. Decreasing the amount of vaporized anesthetic agent output by the vaporizer, and thus delivered to the patient, may be achieved through one or more or each of decreasing the gain to the ultrasonic transducer, as indicated at 322, decreasing the heating element power output, as indicated at 324, and decreasing the valve opening, as indicated at 326.

As one example of the method at 320, the controller may decrease the gain to the ultrasonic transducer, as indicated at 322, while maintaining (e.g., not changing) the heating element power output and the valve opening. By decreasing the gain to the ultrasonic transducer, less kinetic energy may be imparted to the liquid anesthetic agent, resulting in less nebulized anesthetic agent being delivered to the vaporizing chamber. In such an example, the controller may input the anesthetic agent concentration error into one or more look-up tables, algorithms, or functions, which may output an amount to decrease the gain to the ultrasonic transducer. The controller may then decrease the gain to the ultrasonic transducer by the determined amount. In particular, due to the rapid, nearly instantaneous creation of anesthetic agent droplets via powering on of the ultrasonic transducer, varying the transducer duty cycle, frequency, and/or amplitude to adjust the anesthetic agent output may result in a faster control response than adjusting the heating element power output and/or adjusting the valve opening. Therefore, in some examples, the controller may preferentially decrease the gain to the ultrasonic transducer (including adjusting one or more of the transducer duty cycle, frequency, and amplitude) while maintaining the heating element power output and the valve opening.

In a second example of the method at 320, the controller may decrease the heating element power output, as indicated at 324, while maintaining the gain to the ultrasonic transducer and maintaining the valve opening. For example, the heating element power output may be decreased to decrease the amount of vaporized anesthetic agent output by the vaporizer when the ultrasonic transducer is operated to deliver a surplus of nebulized anesthetic agent to the vaporizing chamber. In the second example, the controller may input the anesthetic agent concentration error into one or more look-up tables, algorithms, or functions, which may output an amount to decrease the heating element power output. The controller may then decrease the heating element power output by the determined amount.

In a third example of the method at 320, the controller may decrease the valve opening, as indicated at 326, while maintaining the gain to the ultrasonic transducer and maintaining the heating element power output. By decreasing the valve opening, less vaporized anesthetic agent may be provided to the gas outlet passage (e.g., via venturi 260 shown in FIG. 2). In the third example, the controller may input the anesthetic agent concentration error into one or more look-up tables, algorithms, or functions, which may output an amount to decrease the valve opening. The controller may then adjust the valve opening to decrease the valve opening by the determined amount.

In still other examples of the method at 320, the controller may simultaneously or sequentially decrease at least two of the gain to the ultrasonic transducer, the heating element power output, and the valve opening. For example, the controller may input the anesthetic agent concentration error into one or more look-up tables, algorithms, or functions, which may output a combination of adjustments to the gain to the ultrasonic transducer, the heating element power output, and the valve opening that are expected to bring the anesthetic agent concentration error value within the allowable range. Following 320, method 300 may return.

Returning to 318, if the anesthetic agent concentration error is not greater than zero, method 300 proceeds to 328 and includes increasing the amount of vaporized anesthetic agent output by the vaporizer. Increasing the amount of vaporized anesthetic agent output by the vaporizer, and thus delivered to the patient, may be achieved through one or more or each of increasing the gain to the ultrasonic transducer, as indicated at 330, increasing the heating element power output, as indicated at 332, and increasing the valve opening, as indicated at 334.

As one example of the method at 328, the controller may increase the gain to the ultrasonic transducer, as indicated at 330, while maintaining the heating element power output and the valve opening. By increasing the gain to the ultrasonic transducer, additional kinetic energy may be imparted to the liquid anesthetic agent, resulting in more nebulized anesthetic agent being delivered to the vaporizing chamber. In such an example, the controller may input the anesthetic agent concentration error into one or more look-up tables, algorithms, or functions, which may output an amount to increase the gain to the ultrasonic transducer. The controller may then increase the gain to the ultrasonic transducer by the determined amount. In some examples, the controller may preferentially increase the gain to the ultrasonic transducer (including adjusting one or more of the transducer duty cycle, frequency, and amplitude) while maintaining the heating element power output and the valve opening due to the rapid change in the output anesthetic agent concentration that results from adjusting the ultrasonic transducer gain.

In a second example of the method at 328, the controller may increase the heating element power output, as indicated at 332, while maintaining the gain to the ultrasonic transducer and maintaining the valve opening. For example, the heating element power output may be increased to increase the amount of vaporized anesthetic agent output by the vaporizer when the ultrasonic transducer is operated to deliver a surplus of nebulized anesthetic agent to the vaporizing chamber. In the second example, the controller may input the anesthetic agent concentration error into one or more look-up tables, algorithms, or functions, which may output an amount to increase the heating element power output. The controller may then increase the heating element power output by the determined amount.

In a third example of the method at 328, the controller may increase the valve opening, as indicated at 334, while maintaining the gain to the ultrasonic transducer and maintaining the heating element power output. As an example, the controller may increase the valve opening while maintaining the gain to the ultrasonic transducer and maintaining the heating element power output when the ultrasonic transducer and the heating element are operated to produce a surplus of vaporized anesthetic agent. By increasing the valve opening, a greater amount of vaporized anesthetic agent may be provided to the gas outlet passage. In the third example, the controller may input the anesthetic agent concentration error into one or more look-up tables, algorithms, or functions, which may output an amount to increase the valve opening. The controller may then adjust the valve opening to increase the valve opening by the determined increased amount.

In still other examples of the method at 328, the controller may simultaneously or sequentially increase at least two of the gain to the ultrasonic transducer, the heating element power output, and the valve opening. For example, the controller may input the anesthetic agent concentration error into one or more look-up tables, algorithms, or functions, which may output a combination of adjustments to the gain to the ultrasonic transducer, the heating element power output, and the valve opening that are expected to bring the anesthetic agent concentration error value within the allowable range. Following 328, method 300 may return.

Thus, the systems and methods described herein provide for an ultrasonically driven anesthetic vaporizer system. By including an ultrasonic transducer, a low cost component, to both transport liquid anesthetic agent from a sump and nebulize the liquid anesthetic agent, a cost of the anesthetic vaporizer system may be reduced. Additionally, a size of the anesthetic vaporizer system may be reduced, with fewer components and simplified plumbing. Further, the anesthetic agent may be supplied to a patient with a relatively fast response time due to heating the nebulized liquid anesthetic agent (e.g., via heating a surface of a vaporizing chamber with a heating element) relative to bulk boiling the liquid anesthetic agent. Further still, an amount of the anesthetic agent supplied to the patient may be precisely controlled by adjusting operation of the ultrasonic transducer, the heating element, and/or a flow control valve. In some examples, the operation of the ultrasonic transducer may be adjusted pre-emptively based on a level of the liquid anesthetic agent in the sump to maintain a desired amount of the anesthetic agent supplied to the patient. In other examples, additionally or alternatively, the operation of the ultrasonic transducer may be adjusted in response to the amount of the anesthetic agent supplied to the patient deviating from the desired amount. Overall, the combined control of the ultrasonic transducer, the heating element, and the flow control valve enables precise, high dynamic range, fast-response adjustments to be made to the amount of anesthetic agent supplied to the patient.

A technical effect of using an ultrasonic transducer to nebulize liquid anesthetic agent is that vaporized anesthetic agent may be generated by a low cost, compact anesthesia vaporizer system while the amount of vaporized anesthetic agent provided to a patient may be precisely controlled.

In one embodiment, a system for an anesthesia vaporizer comprises: a sump configured to hold a liquid anesthetic agent; an ultrasonic transducer coupled to a bottom of the sump and at least partially disposed within the sump; a vaporizing chamber fluidically coupled to the sump; and a heating element coupled to the vaporizing chamber and configured to increase a temperature of a surface disposed within the vaporizing chamber. In a first example of the system, the system further comprises a mist transfer tube at least partially disposed within the sump, the ultrasonic transducer coupled within a bottom opening of the mist transfer tube, a top opening of the mist transfer tube extending within the vaporizing chamber; and a vapor delivery passage that fluidically couples the vaporizing chamber to a venturi. In a second example of the system, which optionally includes the first example, the system further comprises a valve disposed within the vapor delivery passage between the vaporizing chamber and the venturi. In a third example of the system, which optionally includes one or both of the first and second examples, an inlet of the venturi is coupled to a gas inlet passage configured to deliver a flow of fresh gas to the venturi, an outlet of the venturi is coupled to a gas outlet passage, and a throat of the venturi is coupled to the vapor delivery passage. In a fourth example of the system, which optionally includes one or more or each of the first through third examples, the system further comprises a controller storing executable instructions in non-transitory memory that, when executed, cause the controller to: operate the ultrasonic transducer at a frequency, a drive amplitude, and/or a duty cycle selected to provide a desired concentration of anesthetic agent in the gas outlet passage. In a fifth example of the system, which optionally includes one or more or each of the first through fourth examples, the system further comprises a concentration sensor coupled to the gas outlet passage, and the controller stores further instructions in non-transitory memory that, when executed, cause the controller to: measure a concentration of anesthetic agent in the gas outlet passage via the concentration sensor; determine an error value between the measured concentration of anesthetic agent and the desired concentration of anesthetic agent; increase the gain to the ultrasonic transducer in response to the error value being less than zero and outside of an allowable range; and decrease the gain to the ultrasonic transducer in response to the error value being greater than zero and outside of the allowable range. In a sixth example of the system, which optionally includes one or more or each of the first through fifth examples, the controller stores further instructions in non-transitory memory that, when executed, cause the controller to: operate the heating element at a power output selected to provide the desired concentration of anesthetic agent in the gas outlet passage. In a seventh example of the system, which optionally includes one or more or each of the first through sixth examples, the heating element is a conductive heating element, and the surface disposed within the vaporizing chamber is generally conical in shape. In an eight example of the system, which optionally includes one or more or each of the first through seventh examples, the heating element is an inductive heating element, and the surface disposed within the vaporizing chamber comprises a metal grid.

In another embodiment, a method for an anesthetic vaporizer comprises: supplying power to a heating element configured to heat a surface of a vaporizing chamber of the anesthetic vaporizer; operating an ultrasonic transducer configured to nebulize liquid anesthetic agent and deliver the nebulized anesthetic agent to the heated surface of the vaporizing chamber; and adjusting an amount of anesthetic agent output by the anesthetic vaporizer based on at least one of a measured concentration of anesthetic agent output by the anesthetic vaporizer and a concentration setpoint. In a first example of the method, adjusting the amount of anesthetic agent output by the anesthetic vaporizer includes adjusting one or more of a frequency, a drive amplitude, and a duty cycle of power supplied to the ultrasonic transducer while operating the ultrasonic transducer. In a second example of the method, which optionally includes the first example, adjusting one or more of the frequency, the drive amplitude, and the duty cycle of power supplied to the ultrasonic transducer while operating the ultrasonic transducer comprises: increasing one or more of the frequency, the drive amplitude, and the duty cycle of power supplied to the ultrasonic transducer as the concentration setpoint increases; decreasing one or more of the frequency, the drive amplitude, and the duty cycle of power supplied to the ultrasonic transducer as the concentration setpoint decreases; increasing one or more of the frequency, the drive amplitude, and the duty cycle of power supplied to the ultrasonic transducer in response to a difference between the measured concentration and the concentration setpoint decreasing below a lower error threshold; and decreasing one or more of the frequency, the drive amplitude, and the duty cycle of power supplied to the ultrasonic transducer in response to the difference between the measured concentration and the concentration setpoint increasing above an upper error threshold. In a third example of the method, which optionally includes one or both of the first and second examples, supplying power to the heating element includes selecting one or more of a voltage and a duty cycle of voltage to supply to the heating element based on a desired temperature of the heated surface, the desired temperature of the heated surface selected based on at least one of the concentration setpoint and a boiling point of the liquid anesthetic agent. In a fourth example of the method, which optionally includes one or more or each of the first through third examples, adjusting the amount of anesthetic agent output by the anesthetic vaporizer based on at least one of the measured concentration of the anesthetic agent output by the anesthetic vaporizer and the concentration setpoint includes adjusting one or more of the voltage and the duty cycle of voltage supplied to the heating element based on a difference between the measured concentration and the concentration setpoint. In a fifth example of the method, which optionally includes one or more or each of the first through fourth examples, adjusting one or more of the voltage and the duty cycle of voltage supplied to the heating element based on the difference between the measured concentration and the concentration setpoint comprises: increasing one or more of the voltage and the duty cycle of voltage supplied to the heating element in response to the difference between the measured concentration and the concentration setpoint decreasing below a lower error threshold; and decreasing one or more of the the voltage and the duty cycle of voltage supplied to the heating element in response to the difference between the measured concentration and the concentration setpoint increasing above an upper error threshold. In a sixth example of the method, which optionally includes one or more or each of the first through fifth examples, adjusting the amount of anesthetic agent output by the anesthetic vaporizer based on at least one of the measured concentration of the anesthetic agent output by the anesthetic vaporizer and the concentration setpoint comprises: increasing an opening of a valve coupled between the vaporizing chamber and an outlet passage of the anesthetic vaporizer as the concentration setpoint increases; decreasing the opening of the valve as the concentration setpoint decreases; increasing the opening of the valve in response to a difference between the measured concentration and the concentration setpoint decreasing below a lower error threshold; and decreasing the opening of the valve in response to the difference between the measured concentration and the concentration setpoint increasing above an upper error threshold.

In another embodiment, a system for an anesthesia machine comprises: an anesthetic vaporizer, the anesthetic vaporizer including a vaporizing chamber coupled to a housing of a sump, the sump and the vaporizing chamber fluidically coupled by a tube that extends from a bottom of the sump to an interior of the vaporizing chamber; an ultrasonic transducer coupled to the bottom of the sump and extending within the tube; a heater coupled to the vaporizing chamber; a vapor delivery passage that fluidically couples the vaporizing chamber to a throat region of a venturi, an inlet of the venturi coupled to a fresh gas flow and an outlet of the venturi coupled to a patient breathing circuit; a valve disposed in the vapor delivery passage; and a controller storing executable instructions in non-transitory memory that, when executed, cause the controller to: operate each of the ultrasonic transducer, the heater, and the valve at a first setpoint to flow vaporized anesthetic agent from the anesthesia machine to the patient breathing circuit; and adjust one or more of the ultrasonic transducer, the heater, and the valve from the first setpoint to a second setpoint based on an electronic feedback signal. In a first example of the system, the electronic feedback signal is an anesthetic agent concentration measured by a concentration sensor coupled between the outlet of the venturi and the patient breathing circuit. In a second example of the system, which optionally includes the first example, the electronic feedback signal is a level of liquid anesthetic agent in the sump measured by a fluid level sensor. In a third example of the system, which optionally includes one or both of the first and second examples, the first setpoint of each of the ultrasonic transducer, the heater, and the valve is selected based on at least one of a concentration setpoint, a mass flow rate of the fresh gas flow, and a type of anesthetic agent.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for an anesthesia vaporizer, comprising: a sump configured to hold a liquid anesthetic agent; an ultrasonic transducer coupled to a bottom of the sump and at least partially disposed within the sump; a vaporizing chamber fluidically coupled to the sump; a heating element coupled to the vaporizing chamber and configured to increase a temperature of a surface disposed within the vaporizing chamber; a mist transfer tube at least partially disposed within the sump, the ultrasonic transducer coupled within a bottom opening of the mist transfer tube, a top opening of the mist transfer tube extending within the vaporizing chamber; and a vapor delivery passage that fluidically couples the vaporizing chamber to a venturi.

2. The system of claim 1, further comprising a valve disposed within the vapor delivery passage between the vaporizing chamber and the venturi.

3. The system of claim 2, wherein an inlet of the venturi is coupled to a gas inlet passage configured to deliver a flow of fresh gas to the venturi, an outlet of the venturi is coupled to a gas outlet passage, and a throat of the venturi is coupled to the vapor delivery passage.

4. The system of claim 3, further comprising a controller storing executable instructions in non-transitory memory that, when executed, cause the controller to:
operate the ultrasonic transducer at a frequency, a drive amplitude, and/or a duty cycle selected to provide a desired concentration of anesthetic agent in the gas outlet passage.

5. The system of claim 4, further comprising a concentration sensor coupled to the gas outlet passage, and wherein the controller stores further instructions in non-transitory memory that, when executed, cause the controller to:
measure a concentration of anesthetic agent in the gas outlet passage via the concentration sensor;
determine an error value between the measured concentration of anesthetic agent and the desired concentration of anesthetic agent;
increase the gain to the ultrasonic transducer in response to the error value being less than zero and outside of an allowable range; and decrease the gain to the ultrasonic transducer in response to the error value being greater than zero and outside of the allowable range.

6. The system of claim 5, wherein increasing gain to the ultrasonic transducer includes increasing the gain while maintaining a power output of the heating element and maintaining the valve open.

7. The system of claim 6, wherein the controller stores further instructions in non-transitory memory that, when executed, cause the controller to input the error value into one or more look-up tables, algorithms, or functions configured to output an amount to increase the gain to the ultrasonic transducer.

8. The system of claim 7, wherein the controller stores further instructions in non-transitory memory that, when executed, cause the controller to increase the gain to the ultrasonic transducer by the determined amount.

9. The system of claim 6, wherein increasing the gain to the ultrasonic transducer includes adjusting one or more of the following: transducer duty cycle, frequency, and amplitude.

10. The system of claim 4, wherein the controller stores further instructions in non-transitory memory that, when executed, cause the controller to:
operate the heating element at a power output selected to provide the desired concentration of anesthetic agent in the gas outlet passage.

11. The system of claim 1, wherein the heating element is a conductive heating element, and the surface disposed within the vaporizing chamber is generally conical in shape.

12. The system of claim 1, wherein the heating element is an inductive heating element, and the surface disposed within the vaporizing chamber comprises a metal grid.

13. A system for an anesthesia machine, comprising:
an anesthetic vaporizer, the anesthetic vaporizer including a vaporizing chamber coupled to a housing of a sump, the sump and the vaporizing chamber fluidically coupled by a tube that extends from a bottom of the sump to an interior of the vaporizing chamber;
an ultrasonic transducer coupled to the bottom of the sump and extending within the tube;
a heater coupled to the vaporizing chamber;
a vapor delivery passage that fluidically couples the vaporizing chamber to a throat region of a venturi, an inlet of the venturi coupled to a fresh gas flow and an outlet of the venturi coupled to a patient breathing circuit;
a valve disposed in the vapor delivery passage; and
a controller storing executable instructions in non-transitory memory that, when executed, cause the controller to:
operate each of the ultrasonic transducer, the heater, and the valve at a first setpoint to flow vaporized anesthetic agent from the anesthesia machine to the patient breathing circuit; and
adjust one or more of the ultrasonic transducer, the heater, and the valve from the first setpoint to a second setpoint based on an electronic feedback signal.

14. The system of claim 13, wherein the electronic feedback signal is an anesthetic agent concentration measured by a concentration sensor coupled between the outlet of the venturi and the patient breathing circuit.

15. The system of claim 14, wherein the electronic feedback signal is a level of liquid anesthetic agent in the sump measured by a fluid level sensor.

16. The system of claim 14, wherein the first setpoint of each of the ultrasonic transducer, the heater, and the valve is selected based on at least one of a concentration setpoint, a mass flow rate of the fresh gas flow, and a type of anesthetic agent.

* * * * *